US008109896B2

(12) United States Patent
Nissan et al.

(10) Patent No.: US 8,109,896 B2
(45) Date of Patent: Feb. 7, 2012

(54) DEVICES AND METHODS FOR OPENING FLUID PASSAGEWAYS (75) Inventors: Oded Nissan, Modiin (IL); Jonathan Ben-Zvi, Tel Aviv (IL); Ira Yaron, Har Adar (IL)

(73) Assignee: Optonol Ltd., Neve Ilan (IL)

( * ) Notice: Subject to any disclaimer, the term of this patent is extended or adjusted under 35 U.S.C. 154(b) by 245 days.

(21) Appl. No.: 12/029,255

(22) Filed: Feb. 11, 2008

(65) Prior Publication Data
US 2009/0204053 A1 Aug. 13, 2009

(51) Int. Cl.
*A61M 5/00* (2006.01)
(52) U.S. Cl. ............................... 604/8; 604/9
(58) Field of Classification Search ........... 604/7–10, 604/264, 521; 623/1.11, 4.1; 606/107–109, 606/153, 167, 184–188
See application file for complete search history.

(56) References Cited

U.S. PATENT DOCUMENTS

| 15,192 | A | 6/1856 | Peale |
|---|---|---|---|
| 274,447 | A | 3/1883 | Kennish |
| 733,152 | A | 7/1903 | Chisholm |
| 1,388,172 | A | 8/1921 | Craddock |
| 2,431,587 | A | 11/1947 | Schnee |
| 2,555,076 | A | 5/1951 | Crossley |
| 2,867,213 | A | 1/1959 | Thomas, Jr. |
| 3,159,161 | A | 12/1964 | Ness |
| 3,272,204 | A | 9/1966 | Artandi et al. |
| 3,310,051 | A | 3/1967 | Schulte |
| 3,333,588 | A | 8/1967 | Schulte |
| 3,421,509 | A | 1/1969 | Fiore |
| 3,530,860 | A | 9/1970 | Majoros |
| 3,589,401 | A | 6/1971 | Harding |
| 3,788,327 | A | 1/1974 | Donowitz et al. |
| 3,884,238 | A | 5/1975 | O'Malley et al. |

(Continued)

FOREIGN PATENT DOCUMENTS
EP 0 102 747 A1 7/1983
(Continued)

OTHER PUBLICATIONS

Prata, João Antonio, Jr., MD, et al., "In Vitro and In Vivo Flow Characteristics of Glaucoma Drainage Implants," Ophthalmology, vol. 102, No. 6, pp. 894-904 (Jun. 1995).

(Continued)

*Primary Examiner* — Tatyana Zalukaeva
*Assistant Examiner* — Benedict L Hanrahan
(74) *Attorney, Agent, or Firm* — Kenyon & Kenyon LLP (57) ABSTRACT

Devices and procedures for assisting drainage of aqueous humor from the eye are provided. In accordance with some embodiments, an implant sized to fit within the Schlemm's Canal is provided. The implant has a plurality of penetrating members having an unextended position in which the penetrating members lie generally close to the longitudinal axis of the implant and an extended position in which the penetrating members are extended outward. In use, the implant is advanced around at least a substantial portion of the Schlemm's Canal with the penetrating members in the first unextended position. After the implant is positioned within the Schlemm's Canal, the penetrating members are caused to move from the first unextended position to the second extended position, wherein the penetrating members penetrate the wall of the Schlemm's Canal. This creates fluid passageways in the wall of the Schlemm's Canal. The implant can also serve to keep the Schlemm's Canal open. A delivery device is also provided for implanting an implant into the Schlemm's Canal.

20 Claims, 7 Drawing Sheets

U.S. PATENT DOCUMENTS

| | | |
|---|---|---|
| 3,890,976 A | 6/1975 | Bazell et al. |
| 3,913,584 A | 10/1975 | Walchle et al. |
| 3,915,172 A | 10/1975 | Wichterle et al. |
| 3,938,529 A | 2/1976 | Gibbons |
| 3,957,035 A | 5/1976 | Chassaing |
| 3,976,077 A | 8/1976 | Kerfoot, Jr. |
| 4,037,604 A | 7/1977 | Newkirk |
| 4,142,526 A | 3/1979 | Zaffaroni et al. |
| 4,153,058 A | 5/1979 | Nehme |
| 4,175,563 A | 11/1979 | Arenberg et al. |
| 4,290,426 A | 9/1981 | Luschen et al. |
| 4,299,227 A | 11/1981 | Lincoff |
| 4,303,063 A | 12/1981 | Stahl |
| 4,402,681 A | 9/1983 | Haas et al. |
| 4,457,757 A | 7/1984 | Molteno |
| 4,474,569 A | 10/1984 | Newkirk |
| 4,521,210 A | 6/1985 | Wong |
| 4,526,343 A | 7/1985 | d'Agostino et al. |
| 4,538,611 A | 9/1985 | Kelman |
| 4,554,918 A | 11/1985 | White |
| 4,563,779 A | 1/1986 | Kelman |
| 4,578,058 A | 3/1986 | Grandon |
| 4,587,954 A | 5/1986 | Haber |
| 4,598,705 A | 7/1986 | Lichtenberger |
| 4,604,087 A | 8/1986 | Joseph |
| 4,634,418 A | 1/1987 | Binder |
| 4,645,493 A | 2/1987 | Ferrando et al. |
| 4,660,546 A | 4/1987 | Herrick et al. |
| 4,692,142 A | 9/1987 | Dignam et al. |
| 4,722,724 A | 2/1988 | Schocket |
| 4,750,901 A | 6/1988 | Molteno |
| 4,750,971 A | 6/1988 | Maas et al. |
| 4,751,926 A | 6/1988 | Sasaki |
| 4,781,675 A | 11/1988 | White |
| 4,787,885 A | 11/1988 | Binder |
| 4,808,183 A | 2/1989 | Panje |
| 4,813,941 A | 3/1989 | Shea |
| 4,826,478 A | 5/1989 | Schocket |
| 4,863,457 A | 9/1989 | Lee |
| 4,886,488 A | 12/1989 | White |
| 4,909,783 A | 3/1990 | Morrison |
| 4,915,684 A | 4/1990 | MacKeen et al. |
| 4,934,363 A | 6/1990 | Smith et al. |
| 4,936,825 A | 6/1990 | Ungerleider |
| 4,942,875 A | 7/1990 | Hlavacek et al. |
| 4,946,436 A | 8/1990 | Smith |
| 4,959,048 A | 9/1990 | Seder et al. |
| 4,964,850 A | 10/1990 | Bouton et al. |
| 4,968,296 A | 11/1990 | Ritch et al. |
| 5,000,731 A | 3/1991 | Wong et al. |
| 5,041,081 A | 8/1991 | Odrich |
| 5,053,040 A | 10/1991 | Goldsmith, III |
| 5,064,417 A | 11/1991 | Andreussi |
| 5,071,408 A | 12/1991 | Ahmed |
| 5,073,163 A | 12/1991 | Lippman |
| 5,092,837 A | 3/1992 | Ritch et al. |
| 5,098,393 A | 3/1992 | Amplatz et al. |
| 5,098,438 A | 3/1992 | Siepser |
| 5,106,367 A | 4/1992 | Ureche et al. |
| 5,127,901 A | 7/1992 | Odrich |
| 5,139,502 A | 8/1992 | Berg et al. |
| 5,147,370 A | 9/1992 | McNamara et al. |
| 5,167,620 A | 12/1992 | Ureche et al. |
| 5,171,213 A | 12/1992 | Price, Jr. |
| 5,171,270 A | 12/1992 | Herrick |
| 5,178,604 A | 1/1993 | Baerveldt et al. |
| 5,190,552 A | 3/1993 | Kelman |
| 5,207,660 A | 5/1993 | Lincoff |
| 5,217,486 A | 6/1993 | Rice et al. |
| 5,221,278 A | 6/1993 | Linkwitz et al. |
| 5,242,449 A | 9/1993 | Zaleski |
| 5,283,063 A | 2/1994 | Freeman |
| 5,300,020 A | 4/1994 | L'Esperance, Jr. |
| 5,318,558 A | 6/1994 | Linkwitz et al. |
| 5,322,504 A | 6/1994 | Doherty et al. |
| 5,326,345 A | 7/1994 | Price, Jr. |
| 5,338,291 A | 8/1994 | Speckman et al. |
| 5,342,370 A | 8/1994 | Simon et al. |
| 5,346,464 A | 9/1994 | Camras |
| 5,355,871 A | 10/1994 | Hurley et al. |
| 5,358,492 A | 10/1994 | Feibus |
| 5,360,398 A | 11/1994 | Grieshaber et al. |
| 5,360,399 A | 11/1994 | Stegmann |
| 5,370,607 A | 12/1994 | Memmen |
| 5,372,577 A | 12/1994 | Ungerleider |
| 5,380,290 A | 1/1995 | Makower et al. |
| D356,867 S | 3/1995 | Krupin |
| 5,397,300 A | 3/1995 | Baerveldt et al. |
| 5,403,323 A | 4/1995 | Smith |
| RE34,998 E | 7/1995 | Langerman |
| 5,433,701 A | 7/1995 | Rubinstein |
| 5,433,714 A | 7/1995 | Bloomberg |
| 5,451,229 A | 9/1995 | Geuder et al. |
| 5,454,796 A | 10/1995 | Krupin |
| 5,476,445 A | 12/1995 | Baerveldt et al. |
| 5,494,484 A | 2/1996 | Feingold |
| 5,520,631 A | 5/1996 | Nordquist et al. |
| 5,522,845 A | 6/1996 | Wenstrom, Jr. |
| 5,558,629 A | 9/1996 | Baerveldt et al. |
| 5,558,630 A | 9/1996 | Fisher |
| 5,601,094 A | 2/1997 | Reiss |
| 5,616,118 A | 4/1997 | Ahmed |
| 5,626,558 A | 5/1997 | Suson |
| 5,626,559 A | 5/1997 | Solomon |
| 5,660,205 A | 8/1997 | Epstein |
| 5,674,286 A | 10/1997 | D'Alessio et al. |
| 5,702,414 A | 12/1997 | Richter et al. |
| 5,704,907 A | 1/1998 | Nordquist et al. |
| 5,709,698 A | 1/1998 | Adams et al. |
| 5,713,844 A | 2/1998 | Peyman |
| 5,720,760 A | 2/1998 | Becker et al. |
| 5,741,292 A | 4/1998 | Mendius |
| 5,800,376 A | 9/1998 | Watson et al. |
| 5,807,240 A | 9/1998 | Muller et al. |
| 5,865,831 A | 2/1999 | Cozean et al. |
| 5,868,697 A | 2/1999 | Richter et al. |
| 5,879,319 A | 3/1999 | Pynson et al. |
| 5,893,837 A | 4/1999 | Eagles et al. |
| 5,968,058 A | 10/1999 | Richter et al. |
| 6,004,302 A | 12/1999 | Brierley |
| 6,007,510 A | 12/1999 | Nigam |
| 6,007,511 A | 12/1999 | Prywes |
| 6,050,970 A | 4/2000 | Baerveldt |
| 6,102,045 A | 8/2000 | Nordquist et al. |
| 6,168,575 B1 | 1/2001 | Soltanpour |
| 6,186,974 B1 | 2/2001 | Allan et al. |
| 6,203,513 B1 | 3/2001 | Yaron et al. |
| 6,221,078 B1 | 4/2001 | Bylsma |
| 6,245,077 B1 | 6/2001 | East et al. |
| 6,264,625 B1 | 7/2001 | Rubenstein et al. |
| 6,280,468 B1 | 8/2001 | Schachar |
| 6,299,640 B1 | 10/2001 | Schachar |
| 6,450,984 B1 | 9/2002 | Lynch et al. |
| 6,464,724 B1 | 10/2002 | Lynch et al. |
| 6,471,666 B1 | 10/2002 | Odrich |
| 6,524,275 B1 | 2/2003 | Lynch et al. |
| 6,533,768 B1 | 3/2003 | Hill |
| 6,544,249 B1 | 4/2003 | Yu et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,682,523 B2 | 1/2004 | Shadduck |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,939,298 B2 | 9/2005 | Brown et al. |
| 6,955,656 B2 | 10/2005 | Bergheim et al. |
| 6,981,958 B1 | 1/2006 | Gharib et al. |
| 6,989,007 B2 | 1/2006 | Shadduck |
| 7,008,396 B1 | 3/2006 | Straub |
| 7,041,077 B2 | 5/2006 | Shields |
| 7,094,225 B2 | 8/2006 | Tu et al. |
| 7,135,009 B2 | 11/2006 | Tu et al. |

| | | |
|---|---|---|
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,220,238 B2 | 5/2007 | Lynch et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 * | 2/2008 | Tu et al. ........ 623/1.11 |
| 7,431,710 B2 * | 10/2008 | Tu et al. ........ 604/8 |
| 7,488,303 B1 | 2/2009 | Haffner et al. |
| 7,563,241 B2 | 7/2009 | Tu et al. |
| 2001/0000527 A1 | 4/2001 | Yaron et al. |
| 2002/0133168 A1 | 9/2002 | Smedley et al. |
| 2002/0143284 A1 | 10/2002 | Tu et al. |
| 2003/0060752 A1 | 3/2003 | Bergheim et al. |
| 2003/0097151 A1 | 5/2003 | Smedley et al. |
| 2003/0229303 A1 | 12/2003 | Haffner et al. |
| 2003/0236484 A1 | 12/2003 | Lynch et al. |
| 2004/0015140 A1 | 1/2004 | Shields |
| 2004/0024345 A1 | 2/2004 | Gharib et al. |
| 2004/0088048 A1 | 5/2004 | Richter et al. |
| 2004/0102729 A1 | 5/2004 | Haffner et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0154946 A1 | 8/2004 | Solovay et al. |
| 2004/0210185 A1 | 10/2004 | Tu et al. |
| 2004/0216749 A1 | 11/2004 | Tu |
| 2004/0225250 A1 | 11/2004 | Yablonski |
| 2004/0254520 A1 | 12/2004 | Porteous et al. |
| 2004/0260228 A1 | 12/2004 | Lynch et al. |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0119601 A9 | 6/2005 | Lynch et al. |
| 2005/0119636 A1 | 6/2005 | Haffner et al. |
| 2005/0165385 A1 | 7/2005 | Simon |
| 2005/0209550 A1 | 9/2005 | Bergheim et al. |
| 2005/0250788 A1 | 11/2005 | Tu et al. |
| 2005/0266047 A1 | 12/2005 | Tu et al. |
| 2005/0271704 A1 | 12/2005 | Tu et al. |
| 2005/0277864 A1 | 12/2005 | Haffner et al. |
| 2006/0032507 A1 | 2/2006 | Tu |
| 2006/0069340 A1 | 3/2006 | Simon |
| 2006/0173397 A1 | 8/2006 | Tu et al. |
| 2006/0200113 A1 | 9/2006 | Haffner et al. |
| 2006/0241749 A1 | 10/2006 | Tu et al. |
| 2007/0010827 A1 | 1/2007 | Tu et al. |
| 2007/0088242 A1 | 4/2007 | Coroneo |
| 2007/0106235 A1 | 5/2007 | Coroneo |
| 2007/0106236 A1 | 5/2007 | Coroneo |
| 2007/0149915 A1 | 6/2007 | Yablonski |
| 2007/0191863 A1 | 8/2007 | De Juan et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2008/0015488 A1 | 1/2008 | Tu et al. |
| 2008/0045878 A1 | 2/2008 | Bergheim et al. |
| 2008/0183121 A2 | 7/2008 | Smedley et al. |
| 2008/0195027 A1 | 8/2008 | Coroneo |
| 2008/0200860 A1 | 8/2008 | Tu et al. |
| 2008/0228127 A1 | 9/2008 | Burns et al. |
| 2008/0234624 A2 | 9/2008 | Bergheim et al. |
| 2009/0036819 A1 | 2/2009 | Tu et al. |
| 2009/0076436 A2 | 3/2009 | Gharib et al. |
| 2009/0137983 A1 | 5/2009 | Bergheim et al. |
| 2009/0138022 A1 | 5/2009 | Tu et al. |
| 2009/0138081 A1 | 5/2009 | Bergheim et al. |
| 2009/0143712 A1 | 6/2009 | Tu et al. |
| 2009/0182421 A1 | 7/2009 | Silvestrini et al. |

FOREIGN PATENT DOCUMENTS

| | | |
|---|---|---|
| EP | 0 228 185 A1 | 7/1987 |
| EP | 0 606 188 A1 | 7/1994 |
| EP | 1 310 222 A2 | 5/2003 |
| FR | 2 721 499 A1 | 12/1995 |
| FR | 2 757 068 A1 | 6/1998 |
| JP | 63-305860 | 12/1988 |
| JP | 3-292953 | 12/1991 |
| JP | 5-115502 | 5/1993 |
| JP | 8-155540 | 6/1996 |
| RU | 1797884 A1 | 2/1993 |
| SU | 1191227 A | 11/1985 |
| WO | 91/08784 A1 | 6/1991 |
| WO | 92/00112 A1 | 1/1992 |
| WO | 93/20783 A1 | 10/1993 |
| WO | 94/02081 A1 | 2/1994 |
| WO | 94/06503 A1 | 3/1994 |
| WO | 94/09837 A1 | 5/1994 |
| WO | 94/13234 A1 | 6/1994 |
| WO | 94/17755 A1 | 8/1994 |
| WO | 94/21443 A1 | 9/1994 |
| WO | 95/35078 A1 | 12/1995 |
| WO | 96/03944 A1 | 2/1996 |
| WO | 96/20742 A1 | 7/1996 |
| WO | 96/36377 A1 | 11/1996 |
| WO | 98/30181 A1 | 7/1998 |
| WO | 99/26567 A1 | 6/1999 |
| WO | 00/64393 A1 | 11/2000 |
| WO | 00/72788 A1 | 12/2000 |
| WO | 2007/087061 A2 | 8/2007 |
| WO | 2008/005873 A2 | 1/2008 |
| WO | 2008/061043 A2 | 5/2008 |
| WO | 2009/012406 A1 | 1/2009 |

OTHER PUBLICATIONS

Krupin, Theodore, et al., "Drainage Implants," Glaucoma, edited by Paul L. Kaufman, MD, et al., Section VII, pp. 9.62-9.75 (1994).
Sidoti, Paul A., MD, et al., "Glaucoma Drainage Implants," Current Opinion in Ophthalmology, vol. 5, No. 11 (1994), 4 pages.
Middleton, John C., et al., "Synthetic Biodegradable Polymers as Medical Devices," Medical Plastics and Biomaterials Magazine—MPB Article Index, Mar. 1998, 14 pages [printed May 18, 1999].
Communication Relating to the Results of the Partial International Search, from PCT/US2009/033049, mailed May 15, 2009.
International Search Report and Written Opinion of the International Searching Authority, from PCT/US2009/033049, mailed Sep. 22, 2009.

* cited by examiner

DEVICES AND METHODS FOR OPENING FLUID PASSAGEWAYS

FIELD OF THE INVENTION

The invention relates to devices and methods for assisting drainage of aqueous humor from the eye to treat glaucoma.

BACKGROUND OF THE INVENTION

Glaucoma is an eye condition typically characterized by an increase in the intraocular pressure (IOP) of the eye to an abnormal level. A normal eye maintains a proper IOP by the circulation within the eye of aqueous humor. Aqueous humor is secreted from the ciliary body, passes through the pupil into the anterior chamber of the eyeball, and is filtered out of the eyeball via the trabeculum and the Canal of Schlemm (or Schlemm's Canal). With glaucoma, the aqueous humor excretory pathway is blocked, the aqueous humor cannot pass out of the eyeball at an adequate rate, the IOP rises, the eyeball becomes harder, and the optic nerve atrophies by the pressure applied on its fibers leaving the retina. A characteristic optic neuropathy develops, resulting in progressive death of the ganglion cells in the retina, restriction of the visual field, and eventual blindness. Advanced stages of the disease are characterized also by significant pain.

Glaucoma treatment, if initiated early in the course of the disease, can prevent further deterioration and preserve most of the ocular functions. The goal of glaucoma treatment is to reduce the IOP to a level which is considered safe for a particular eye, but which is not so low as to cause ocular malfunction or retinal complications.

In the past, procedures and devices have been developed and implemented for providing an alternate route for aqueous humor to pass out of the eye. For example, in full thickness filtration surgery, a fistula is created through the limbal sclera, connecting directly the anterior chamber of the eyeball and the sub-conjunctival space. This provides an alternate route allowing the aqueous humor to exit the anterior chamber of the eyeball through the fistula in the limbal sclera and to pass into the sub-conjunctival space. In guarded filtration surgery (trabeculectomy), a fistula created through the limbal sclera is protected by an overlying partial thickness sutured scleral flap. Again, this provides an alternate route allowing the aqueous humor to exit the anterior chamber of the eyeball, through the fistula in the limbal sclera, and allowing the aqueous humor to pass into the sub-conjunctival space.

Drainage implant devices have also been developed and implemented. For example, some implants have a tube that is inserted through the limbal sclera. The tube provides an alternate route for the aqueous humor to leave the eye.

Many of these known devices and methods do not provide adequate regulation of IOP. For example, with some devices and methods, the initial procedure can cause excessive loss of aqueous humor from the eyeball during the early postoperative period, frequently leading to hypotony. With other devices and methods, there may be too much resistance to the flow of aqueous humor from the eyeball, thereby resulting in higher eventual IOP and an increased risk of late failure. There is also the risk that the drainage pathway will become clogged due to scarring or that infection could occur because of the passageway into the eye. In certain valved implant devices, defects in and/or failure of the valve mechanisms can lead to either too much or too little aqueous humor exiting the eye. In procedures that drain into a "bleb" in the sub-conjunctival space, there is sometimes a risk of leakage or infection.

In order to provide improved IOP regulation, some alternative procedures and devices have been proposed to attempt to utilize the eye's natural physiological drainage pathway through the Schlemm's Canal. If the cause of the rise in IOP is a blockage of flow through the trabecular meshwork between the anterior chamber and the Schlemm's Canal, then a device or procedure that opens one or more passageways through the trabecular meshwork or provides a bypass route from the anterior chamber to the Schlemm's Canal can help reduce IOP. To date, none of the procedures or devices that have been proposed to enhance flow from the anterior chamber to the Schlemm's Canal has proven completely satisfactory.

In a deep sclerectomy, a superficial flap is made in the sclera and then a second deep scleral flap is created and excised leaving a scleral reservoir under the first flap. A thin permeable membrane is exposed between the anterior chamber and the scleral reservoir. The procedure is non-penetrating in that no penetration is made into the anterior chamber. The aqueous humor percolates from the anterior chamber through the thin membrane into the scleral reservoir and into the Schlemm's Canal. This procedure can be difficult to perform and has not been shown to be fully effective in reducing IOP.

Trabeculoplasty procedures are a group of procedures where a physician uses a laser to create holes in the trabecular meshwork to allow flow from the anterior chamber into the Schlemm's Canal. The two primary types of trabeculoplasty are argon laser trabeculoplasty (ALT) and selective laser trabeculoplasty (SLT). Trabeculoplasty may not be a suitable long-term treatment as the meshwork may close again, for example due to scarring.

The TRABECTOME™ device of NeoMedix, Inc., has been proposed as another method for providing passage through the trabecular meshwork. The device is passed through a corneal incision and across the anterior chamber. The device's tip has a bipolar micro-electrocautery electrode that ablates and removes a strip of trabecular meshwork. As with trabeculoplasty, this procedure may not be a suitable long-term treatment as the meshwork may close again.

The viscocanalostomy procedure uses a viscoelastic material in a procedure similar to the deep sclerectomy procedure. The physician injects a viscoelastic material, such as sodium hyaluronate, into the Schlemm's Canal from the scleral reservoir. The viscoelastic material opens the Schlemm's Canal and helps to insure the patency of the passage from the scleral reservoir to the Schlemm's Canal. The viscoelastic material is claimed to increase the permeability into the Schlemm's Canal and to help prevent closure of the passage due to fibrongen migration and scarring. Like the deep sclerectomy procedure, the viscocanalostomy procedure can be difficult to perform and has not been proven to be fully effective in reducing IOP.

Canaloplasty is a procedure similar to viscocanalostomy with the primary difference being that viscocanalostomy attempts to open only portions of the Schlemm's Canal adjacent the scleral reservoir, while canaloplasty attempts to open the entire length of the Schlemm's Canal. In canaloplasty, a microcannula is inserted into the Schlemm's Canal at the sceral reservoir and passed all the way around the Schlemm's Canal, in conjunction with the injection of a viscoelastic material around the Schlemm's Canal. A suture is then tied to the microcannula, and the microcannula is withdrawn back around the Schlemm's Canal, pulling the suture through the Schlemm's Canal. The suture is tied together at its ends to apply pressure, stretching the trabecular meshwork inwards and helping open the Schlemm's Canal. Like viscocanalostomy, the canaloplasty procedure can be difficult to perform and has not been proven to be fully effective in reducing IOP.

Two devices that have been proposed to help flow into the Schlemm's Canal are the iStent device of Glaukos Corp. and the EyePass device of GMP Companies, Inc. The iStent device is inserted into the Schlemm's Canal by an ab-interno procedure, while the EyePass is inserted into the Schlemm's Canal by an ab-externo procedure.

The iStent device of Glaukos Corp. is a small L-shaped titanium tube that is implanted through the trabecular meshwork into the Schlemm's Canal. Multiple implants may be used around the circumference of the Schlemm's Canal. The iStent device does not appear to be fully effective in reducing IOP without the need for several implants.

The EyePass device of GMP Companies, Inc., is a small, generally Y-shaped silicon tube that is used in a procedure similar to deep sclerectomy, without the need for the creation of the thin membrane for percolation of aqueous humor from the anterior chamber to the scleral reservoir. The EyePass device is placed in the scleral reservoir with its inlet branch entering the anterior chamber and its two outlet branches passing into the Schlemm's Canal. The EyePass device does not appear to be fully effective in consistently reducing IOP.

None of the known devices or procedures provides a fully satisfactory solution in terms of consistently achieving optimal IOP in an efficient manner.

SUMMARY OF THE INVENTION

The invention provides innovative devices and procedures for assisting drainage of aqueous humor from the eye to treat glaucoma.

In accordance with some embodiments of the invention, an implant is provided for assisting drainage of aqueous humor from the eye, the implant being sized to fit within the Schlemm's Canal of the eye, the implant having a longitudinal axis and comprising a plurality of penetrating members. Each of the penetrating members has a first unextended position in which said penetrating member lies generally close to the longitudinal axis of the implant and a second extended position in which the penetrating member is extended outward to be farther away from the longitudinal axis of the implant.

In use, the implant is inserted into the Schlemm's Canal through an access opening and advanced around at least a substantial portion of the Schlemm's Canal with the penetrating members in the first unextended position. After the implant is positioned within the Schlemm's Canal, the penetrating members are caused to move from the first unextended position to the second extended position, wherein the penetrating members penetrate the wall of the Schlemm's Canal. This creates fluid passageways in the wall of the Schlemm's Canal, which may be in the direction of the anterior chamber and/or in the direction of the scleral spur. The implant may also serve to keep the Schlemm's Canal open in its axial direction and in its radial direction.

The implant may comprises a longitudinally flexible body. The longitudinally flexible body may comprise one or more longitudinally flexible rods. The penetrating members may lie substantially in a single plane when the penetrating members are in the first unextended position.

Each penetrating member may comprise at least one penetrating tip. Each penetrating member may further comprise at least one supporting arm connecting the penetrating tip to the longitudinally flexible body at a hinge. The penetrating members and the longitudinally flexible body may lie substantially in a single plane when the penetrating members are in the first unextended position.

The penetrating members may be configured to self-expand from the first unextended position to the second extended position. The penetrating members may comprise a resilient material, wherein in an unconstrained state the penetrating members are in the second extended position, and wherein in a constrained state the penetrating members are held in the first unextended position. A sheath may be provided around the implant wherein the sheath holds the penetrating members in the first unextended position. Withdrawing the sheath releases the penetrating members allowing them to move from the first unextended position to the second extended position. Alternatively, the penetrating members may comprise a shape memory material, wherein the heat from the eye causes the penetrating members to move from the first unextended position to the second extended position.

The implant may comprise a deployment rod attached to the penetrating members, wherein actuation of the deployment rod causes the penetrating members to move from the first unextended position to the second extended position. Actuation of the deployment rod may be performed by moving the deployment rod relative to the longitudinally flexible body.

The implant may be configured such that when the penetrating members are in the first unextended position, the penetrating members generally point in a proximal direction along the longitudinal axis of the implant. In this configuration, advancing the implant in a distal direction does not cause the penetrating members to become extended. However, retraction the implant in a proximal direction back through the Schlemm's Canal causes the penetrating members to catch on the wall of the Schlemm's Canal. Further retraction of the implant in the proximal direction causes the penetrating members to move from the first unextended position to the second extended position.

The implant may be coated with a drug that elutes from the surface of the implant. The drug may be used, for example, for treating glaucoma, local infections, or another eye disease.

In accordance with other embodiments of the invention, a delivery device is provided for implanting an implant for assisting drainage of aqueous humor from the eye. The delivery device may comprise a generally longitudinally extending shaft, a hooked end with a piercing tip extending generally perpendicular to the shaft, and a lumen passing through the longitudinally extending shaft and the hooked end for accommodating an implant. The delivery device may further comprises one or more lumens for viscoelastic injection, an imaging device, a light source, an operating instrument such as a blade, scissors, coagulator, forceps and/or needle, and/or irrigation.

In accordance with other embodiments of the invention, a method is provided for implanting an implant for assisting drainage of aqueous humor from the eye. The method comprises providing an implant sized to fit within the Schlemm's Canal of the eye, the implant having a longitudinal axis and a plurality of penetrating members. Each of said penetrating members has a first unextended position and a second extended position. The method includes forming an access opening into the Schlemm's Canal, inserting the implant into the Schlemm's Canal through the access opening, advancing the implant around at least a substantial portion of the Schlemm's Canal with the penetrating members in the first unextended position, and causing the penetrating members to move from the first unextended position to the second extended position, wherein the penetrating members penetrate the wall of the Schlemm's Canal.

The access opening into the Schlemm's Canal may be formed ab externo under a scleral flap or ab interno by forming an incision in the cornea and accessing the Schlemm's canal from through the anterior chamber of the eye. The implant may be delivered to the opening in the Schlemm's canal by a delivery device as described above. The penetrating members may be caused to move from the first unextended position to the second extended position by one or more of the mechanisms described above.

The above summary is not meant to be limiting. The invention is defined by the claims appended hereto. Example embodiments are provided in the accompanying drawings and described in the detailed description given below. These are provided as examples only, as other embodiments of the invention come within the scope of the appended claims.

DETAILED DESCRIPTION

Figure 1:
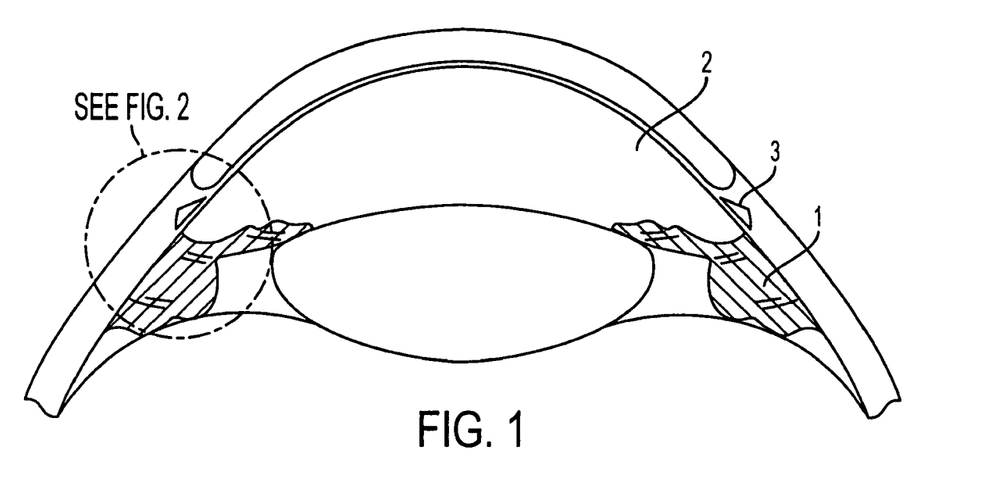
FIG. 1 is a schematic view of an anterior portion of an eye.

FIG. 1 illustrates a schematic view of an anterior portion of an eye. In a normal eye, aqueous humor is secreted from the ciliary body 1, passes through the pupil into the anterior chamber 2, and is filtered out of the eyeball via the trabeculum and the Schlemm's Canal 3. As shown in FIG. 1, the Schlemm's Canal 3 generally encircles the anterior chamber 2 of the eye. As shown in the enlarged view of FIG. 2, in passing from the anterior chamber 2 to the Schlemm's Canal 3, the aqueous humor passes through the trabecular meshwork 4.

Figure 2:
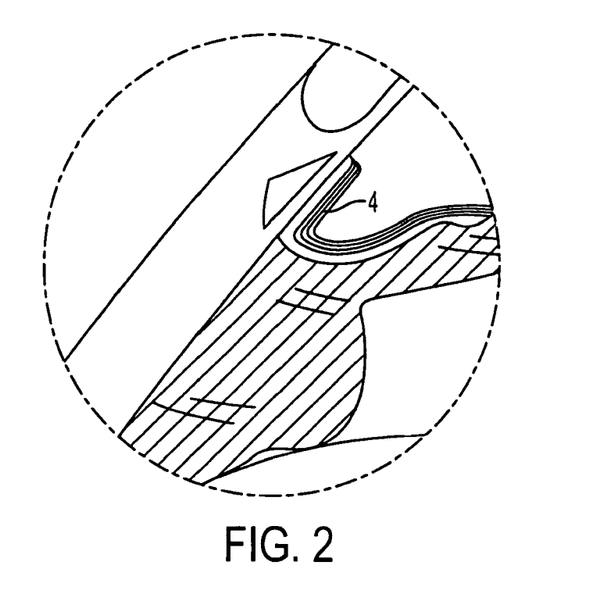
FIG. 2 is an enlarged view of the portion of the eye labeled A in FIG. 1.

A common cause of glaucoma is blockage of flow through the trabecular meshwork 4. When the aqueous humor excretory pathway is blocked, the aqueous humor cannot pass out of the eyeball at an adequate rate, the IOP rises, and glaucoma can develop.

FIGS. 3-13 illustrate a first embodiment of an implant designed to be implanted inside the Schlemm's Canal to open fluid passageways through the wall of the Schlemm's Canal. The implant 10 in this embodiment has a longitudinally flexible body comprising one or more longitudinally flexible rods 11. In the version illustrated in FIGS. 3-13, the implant 10 has two longitudinally flexible rods 11. The longitudinally flexible rods 11 may be constructed of wire or may be wire-like. The rods 11 are longitudinally flexible to allow the implant to be threaded through the Schlemm's Canal, as described in further detail below.

The implant 10 as illustrated in FIGS. 3-13 has a series of penetrating members attached to the longitudinally flexible body. In this embodiment, each penetrating member comprises at least one supporting arm 13 and at least one penetrating tip 14. In this illustrated example, each penetrating tip 14 is connected to the longitudinally flexible body by two supporting arms 13, with each of the two supporting arms 13 extending between the penetrating tip 14 and the longitudinally flexible body and connected to the longitudinally flexible body at a hinge 12.

Figure 3:
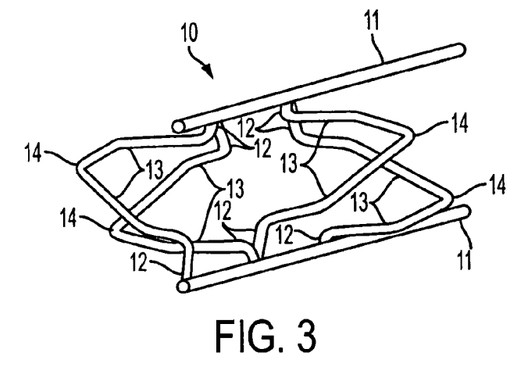
FIG. 3 is a perspective view of a first embodiment of an implant with the penetrating members shown in an extended position.
Figure 4:
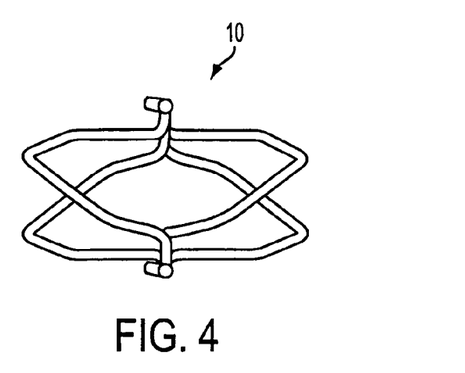
FIG. 4 is an end view of the implant of FIG. 3.
Figure 5:
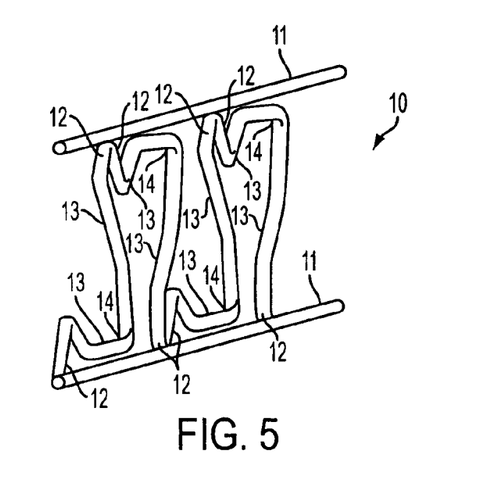
FIG. 5 is a perspective view of the implant of FIG. 3 with the penetrating members shown in an unextended position.
Figure 6:
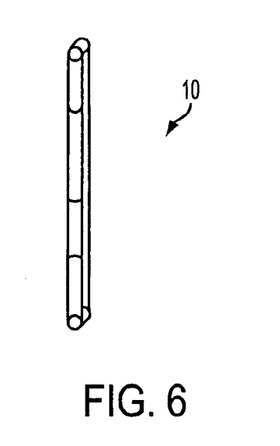
FIG. 6 is an end view of the implant of FIG. 5.

FIGS. 3 and 4 show the implant 10 with the penetrating members in an extended position. FIGS. 5 and 6 show the implant 10 with the penetrating members in an unextended position. As illustrated in FIGS. 5 and 6, when the penetrating members are in the unextended position, the penetrating members and the longitudinally flexible body lie substantially in a single plane. Thus, in this example, when the supporting arms 13 and penetrating tips 14 are in the unextended position, the supporting arms 13 and penetrating tips 14 and the longitudinally flexible rods 11 all lie substantially in a single plane. This can be seen in the end view of FIG. 6. In certain instances, the flexible rods may be closer together or further apart than illustrated. For example, the angles formed by the supporting arms may be smaller, allowing the flexible rods to be closer together. If the angle is small enough, when the supporting arms are unextended the supporting arms and flexible rods may all lie close together and extend in substantially the same direction. Thus, the end view of the implant may resemble a single rod.

Figure 7:
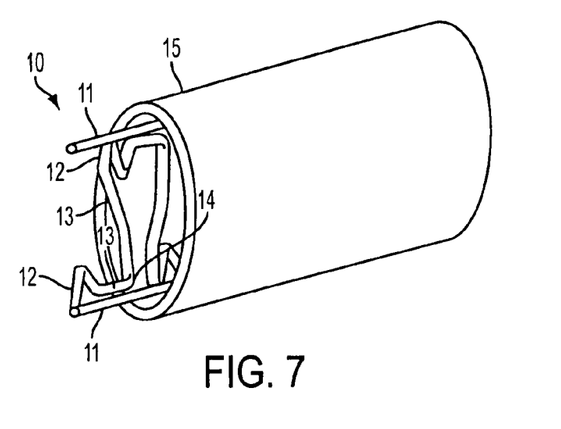
FIG. 7 is a perspective view of the implant of FIG. 5 with the implant inside a delivery sheath.
Figure 8:
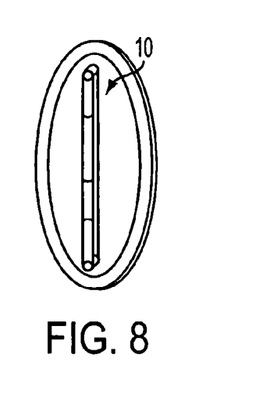
FIG. 8 is an end view of the implant and delivery sheath of FIG. 7.

In the embodiment of FIGS. 3-13, the penetrating members may be configured to self-expand from the unextended position to the extended position. The penetrating members may comprise a resilient material, wherein in an unconstrained, relaxed state the penetrating members are in the extended position as shown in FIGS. 3 and 4. The implant 10 may be manufactured in this condition. As shown in FIGS. 7 and 8, a guiding sheath 15 may be provided to hold the penetrating members in a constrained state, holding the penetrating members in the first unextended position. FIGS. 7 and 8 show the guiding sheath 15 only schematically. It will be appreciated that the guiding sheath 15 may be configured to fit snugly around the implant 10 so as to hold the penetrating members in the unextended condition as shown in FIGS. 5 and 6.

In use, the implant 10 within the guiding sheath 15 is inserted into the Schlemm's Canal through an access opening. The access opening into the Schlemm's Canal may be formed ab externo under a scleral flap or ab interno by forming an incision in the cornea and accessing the Schlemm's canal from through the anterior chamber of the eye. The ab externo procedure may be similar to a deep sclerectomy. A superficial flap may be made in the sclera and then a second deep scleral flap may be created and excised leaving a scleral reservoir under the first flap. An access opening to the Schlemm's Canal can be exposed at the scleral reservoir. Alternatively, a single scleral flap may be made to access the Schlemm's Canal, with or without excising any portion of the sclera.

Figure 9:
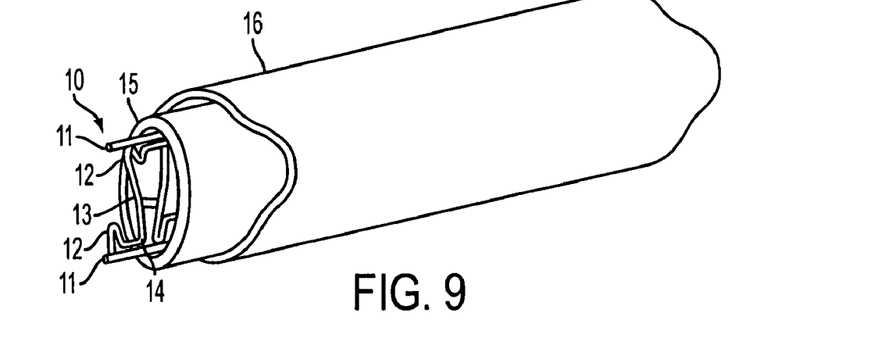
FIG. 9 is a perspective view of the implant and delivery sheath of FIG. 7 being inserted within the Schlemm's Canal.

FIG. 9 is a perspective view of the implant 10 and guiding sheath 15 being inserted within the Schlemm's Canal 16. The implant 10 and guiding sheath 15 are advanced around at least a substantial portion of the Schlemm's Canal, with the penetrating members being held in the unextended position. In certain embodiments, the implant 10 and guiding sheath 15 are advanced substantially 360 degrees around the Schlemm's Canal so that the distal end of the implant 10 reaches the area of the opening into which the implant 10 was inserted. In alternative embodiments, the implant 10 and guiding sheath 15 are advanced only part way around the Schlemm's Canal. In these instances, other implants may be used in other areas of the Schlemm's Canal.

As an alternative method of advancing the implant around at least a substantial portion of said Schlemm's Canal, a guide wire or strand may first be inserted into the Schlemm's Canal. The guide wire or strand may be advanced around the Schlemm's Canal such that its leading end emerges again from the Schlemm's Canal at the area of the access opening. The implant may then be attached to the guide wire or strand. The guide wire or strand may then be withdrawn back through the Schlemm's Canal, thereby pulling the implant into the Schlemm's Canal. Before, during or after threading the implant through the Schlemm's canal, a viscoelastic material, such as sodium hyaluronate, may be injected into the Schlemm's Canal as is known in the art. The viscoelastic material can help open the Schlemm's Canal and help to insure the patency of the Schlemm's Canal.

Figure 10:
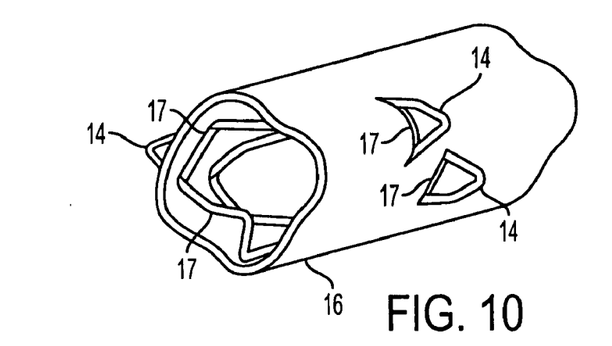
FIG. 10 is a perspective view of the implant of FIG. 7 inside the Schlemm's Canal after withdrawal of the delivery sheath and deployment of the penetrating members to the extended position.
Figure 11:
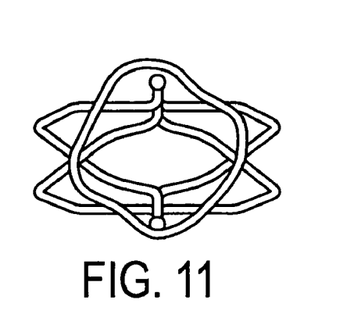
FIG. 11 is an end view of the implant of FIG. 10 within the Schlemm's Canal.

After the implant 10 and guiding sheath 15 is positioned within the Schlemm's Canal, the guiding sheath 15 is withdrawn. This removes the constraint from the penetrating members, allowing them to expand to their expanded position, as shown in FIGS. 10 and 11. As shown in FIGS. 10 and 11, when the penetrating members move from the unextended position to the extended position, the penetrating members penetrate the wall of the Schlemm's Canal 16. This creates fluid passageways or openings 17 in the wall of the Schlemm's Canal 16.

As will be appreciated by persons of ordinary skill in the art, the placement of the implant within the Schlemm's Canal can serve to keep the Schlemm's Canal open. In this regard, the implant can serve as a support scaffolding to maintain the patency of the Schlemm's Canal. In embodiments in which the implant is somewhat larger than the inner size of the Schlemm's Canal, the deployed implant may apply a tension force to the tissue and increase its permeability for fluid flow.

As will also be appreciated by persons of ordinary skill in the art, the implant can have penetrating members on both sides of the Schlemm's Canal. Thus, the penetrating members can create fluid passageways both into the Schlemm's Canal through the trabecular meshwork and also out of the Schlemm's Canal to the collector channels and into the sclera. The penetrating members may differ from those illustrated. For example, each penetrating member may have only a single supporting arm. The supporting arm may have an enlarged or hooked end, such as a hooked end forming a V-shape similar to the ends of the penetrating members as illustrated. The supporting arms alternatively may be in the form of tubes providing a conduit for fluid flow, as discussed further below in conjunction with FIGS. 28 and 29.

At the conclusion of the implantation procedure, if an ab externo procedure is used, the sceral flap may be sutured closed. If an ab interno procedure is used, the opening in the cornea may be sutured closed at the conclusion of the procedure. The procedure also may be performed without suturing.

An alternative self-expansion mechanism that may be used for the implant involves shape memory material. The implant, or portions of the implant may be made of a shape memory material. Using known shape memory material manufacturing techniques, the implant may be manufactured such that the heat from the eye causes the penetrating members to move from the first unextended position to the second extended position.

For use in the Schlemm's Canal as described, the implant must be sized to fit within the Schlemm's Canal. For example, when the penetrating members are in the unextended position, the cross-sectional profile of the implant may have a height from about 0.05 mm to about 1 mm and a width from about 0.015 mm to about 0.25 mm, but other dimensions are of course possible within the scope of the invention. When the penetrating members are in the extended position, the cross-sectional profile of the implant may have a width from about 0.03 mm to about 1 mm, again with other dimensions of course being possible within the scope of the invention. In instances where the implant is designed to extend 360 degrees around the Schlemm's Canal, the implant may in certain examples have a length of about 35 mm or greater. In other instances, the length may be shorter. As just one of many possible examples, the length may be from about 1 mm to about 10 mm such that the implant extends only part way around the Schlemm's Canal.

It will be appreciated that the implant can be described as having a longitudinal axis extended generally down the geometric center of the implant. In the implant 10 of FIGS. 3-13, for example, the longitudinal axis is an imaginary line midway between the two longitudinally flexible rods 11. The penetrating members can therefore be described relative to the longitudinal axis. The penetrating members have an unextended position in which the penetrating members lie generally close to the longitudinal axis of the implant and an extended position in which the penetrating members are extended outward to be farther away from the longitudinal axis of the implant.

Figure 12:
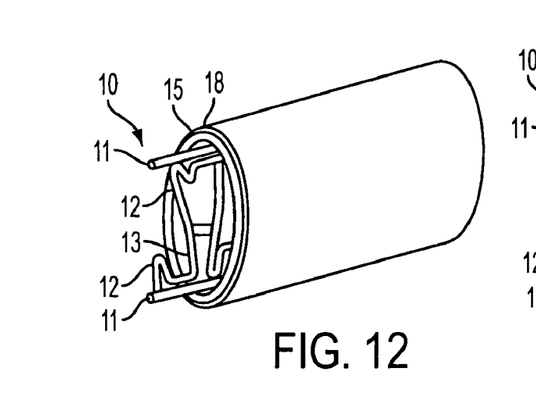
FIG. 12 is a perspective view of the implant and delivery sheath of FIG. 7 inside an ultrasonic guide tube.

FIG. 12 is a perspective view of the implant 10 and guiding sheath 15 inside an ultrasonic guide tube 18. The ultrasonic guide tube 18 uses ultrasound to emulsify tissue in the Schlemm's Canal ahead of the advancing implant in order to help facilitate the implantation procedure and/or open the Schlemm's Canal. In one embodiment, the ultrasonic guide tube 18 has two layers, an inner layer which leads the ultrasonic signal from the ultrasound transducer outside the eye to the tissue on the inner wall of Schlemm's Canal, and an outer layer made of a covering material that blocks the ultrasound signal from reaching the wall of Schlemm's Canal at any place other than the leading end of the inner layer. The inner layer may be slightly longer than the outer layer to provide an exposed area for the leading end of the inner layer to be in contact with the tissue to be emulsified. When the surgeon pushes the guide tube 18 into the Schlemm's Canal, the distal end of the inner tube transfers the ultrasound signal to the tissue causing its emulsification.

Figure 13:
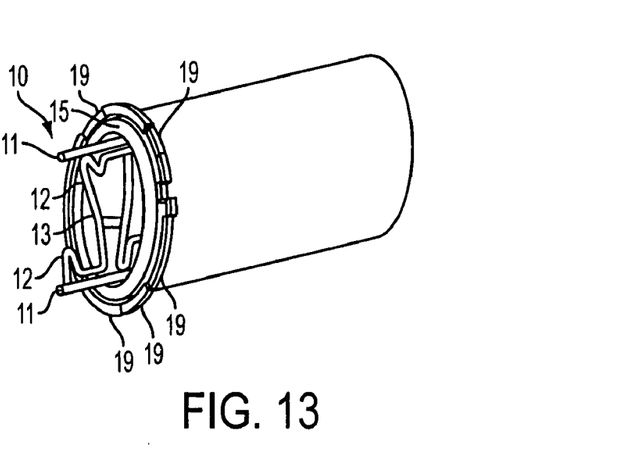
FIG. 13 is a perspective view of the implant and delivery sheath of FIG. 7 inside a cleaning guide tube.

FIG. 13 is a perspective view of the implant 10 and guiding sheath 15 inside a cleaning guide tube 19. The cleaning guide tube 19 has a coarse area on its outer surface at its distal end. When the surgeon pushes the cleaning guide tube into the Schlemm's Canal, the coarse end mechanically removes cells from the inner wall of the Schlemm's Canal. Similar to the ultrasonic guide tube 18, the cleaning guide tube 19 helps facilitate the implantation procedure and/or open the Schlemm's Canal.

FIGS. 14-21 illustrate a second embodiment of an implant, designated as implant 20, designed to be implanted inside the Schlemm's Canal to open fluid passageways through the wall of the Schlemm's Canal. As with implant 10, the implant 20 has a longitudinally flexible body comprising two longitudinally flexible rods 21. Again, the longitudinally flexible rods 21 may be constructed of wire or may be wire-like and are longitudinally flexible to allow the implant to be threaded through the Schlemm's Canal.

The implant 20 has a series of penetrating members, with each penetrating member having two supporting arms 23 and a penetrating tip 24. The supporting arms 23 are hingedly connected to the flexible rods 21 at hinges 22. Each supporting arm 23 extends between its respective penetrating tip 24 and its respective longitudinally flexible rod 21 and is connected to its respective the longitudinally flexible rod at the hinge 22.

The implant 20 has a deployment rod 25 attached to the penetrating members. The deployment rod 25 may be constructed of wire or may be wire-like and is longitudinally flexible to allow the implant to be threaded through the Schlemm's Canal. The deployment rod 25 may also be in the form of a suture.

Figure 14:
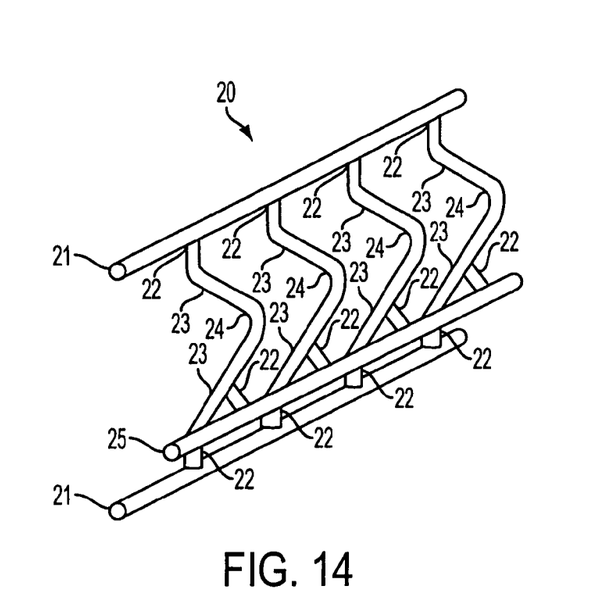
FIG. 14 is a perspective view of a second embodiment of an implant with the penetrating members shown in an unextended position.
Figure 15:
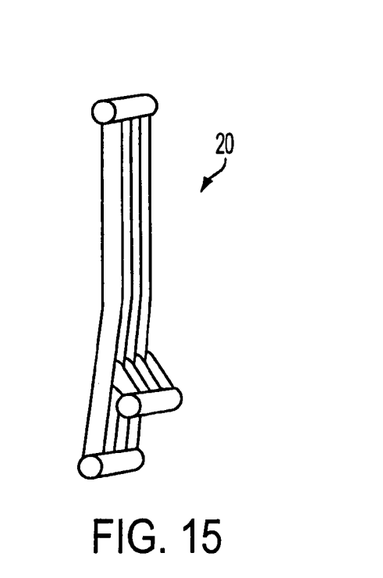
FIG. 15 is an end view of the implant of FIG. 14.
Figure 16:
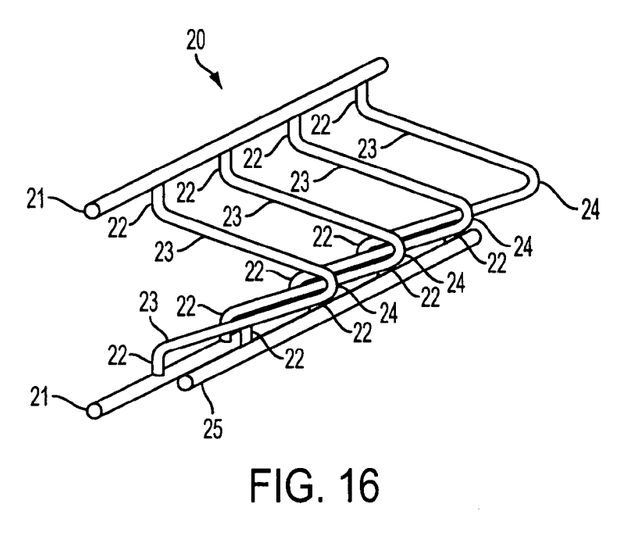
FIG. 16 is a perspective view of the implant of FIG. 14 with the penetrating members shown in an extended position.
Figure 17:
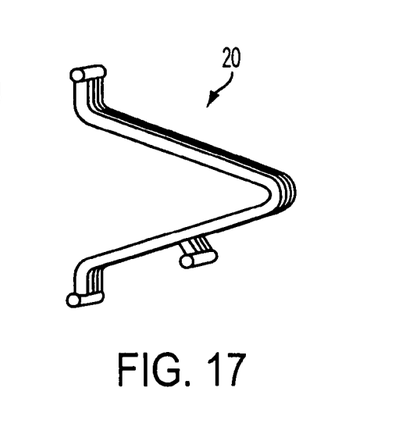
FIG. 17 is an end view of the implant of FIG. 16.

FIGS. 14 and 15 show the implant 20 with the penetrating members in an unextended position. FIGS. 16 and 17 show the implant 20 with the penetrating members in an extended position. As illustrated in FIGS. 14 and 15, when the penetrating members are in the unextended position, the penetrating members and the longitudinally flexible body lie substantially in a single plane. Thus, in this example, when the supporting arms 23 and penetrating tips 24 are in the unextended position, the supporting arms 23, the penetrating tips 24, the longitudinally flexible rods 21, and the deployment rod 25 all lie substantially in a single plane. This can be seen in the end view of FIG. 15. As discussed above, the flexible rods may be closer together or further apart than illustrated, and the angles formed by the supporting arms may differ. When the supporting arms are unextended, the supporting arms and flexible rods may all lie close together and extend in substantially the same direction, resulting in an end view of the implant resembling a single rod.

Figure 18:
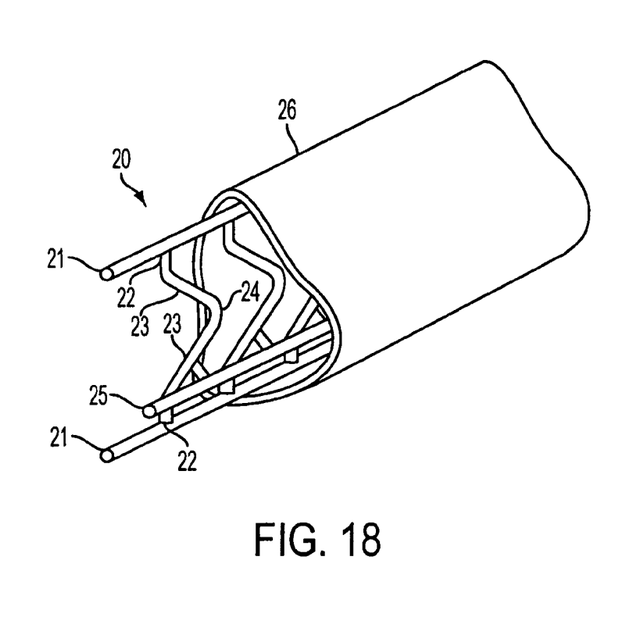
FIG. 18 is a perspective view of the implant of FIG. 14 being inserted within the Schlemm's Canal.
Figure 19:
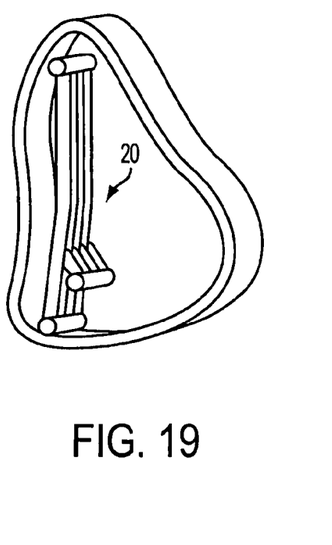
FIG. 19 is an end view of the implant of FIG. 18 within the Schlemm's Canal.

In the implant 20 of FIGS. 14-21, the penetrating members are not self-expanding but instead are designed to be deployed by the deployment rod 25. In use, the implant 20 is inserted into the Schlemm's Canal through an access opening, which may be formed ab externo or ab interno as described above. FIGS. 18 and 19 illustrate the implant 20 being inserted within the Schlemm's Canal 26.

As with the implant 10, the implant 20 is advanced around at least a substantial portion of the Schlemm's Canal. In this embodiment, the penetrating members are in the unextended position in their relaxed state as manufactured, so there is no need for a sheath to hold the penetrating members in the unextended position. Again, as with implant 10, implant 20 may be advanced substantially 360 degrees around the Schlemm's Canal or only part way around the Schlemm's Canal, in which case multiple implants may be used.

After the implant 20 is positioned within the Schlemm's Canal, the penetrating members are moved from the unextended position to the extended position by actuation of the deployment rod 25. Actuation of the deployment rod 25 is performed by moving the deployment rod 25 relative to the longitudinally flexible body. For example, in the illustrated embodiment, the longitudinally flexible rods 21 are held in place while the deployment rod is pulled proximally relative to the longitudinally flexible rods 21. As can be appreciated from FIGS. 14-17, this action causes the penetrating members to rotate at hinges 22 to move to the extended position shown in FIGS. 16-17. The hinging motion causes plastic deformation of the implant 20 so that the penetrating members remain in the extended position after the deployment rod 25 is released.

Figure 20:
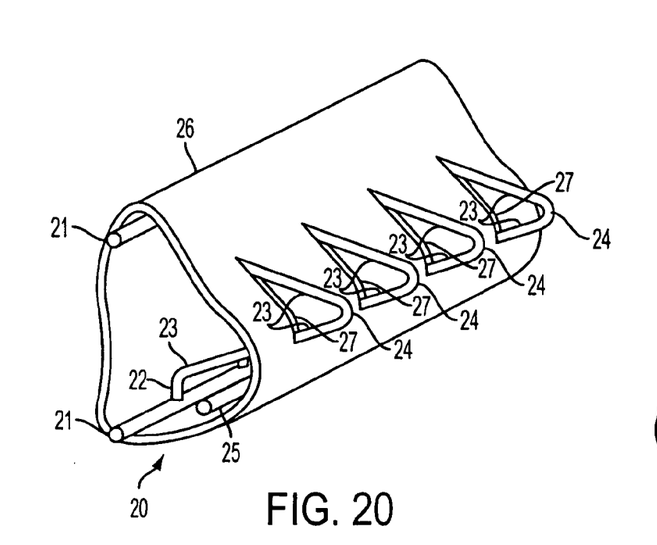
FIG. 20 is a perspective view of the implant of FIG. 18 inside the Schlemm's Canal after deployment of the penetrating members to the extended position.
Figure 21:
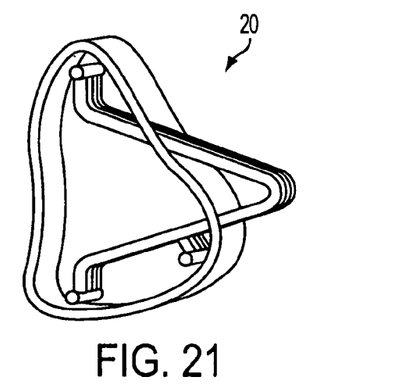
FIG. 21 is an end view of the implant of FIG. 20 within the Schlemm's Canal.

As shown in FIGS. 20 and 21, when the penetrating members move from the unextended position to the extended position, the penetrating members penetrate the wall of the Schlemm's Canal 26. This creates fluid passageways or openings 27 in the wall of the Schlemm's Canal 26.

As with implant 10, the placement of the implant 20 within the Schlemm's Canal can serve to keep the Schlemm's Canal open. In this regard, the implant can serve as a support scaffolding to maintain the patency of the Schlemm's Canal. The size of the implant 20 may be similar to that of implant 10.

FIGS. 22-27 illustrate a third embodiment of an implant, designated as implant 30, designed to be implanted inside the Schlemm's Canal to open fluid passageways through the wall of the Schlemm's Canal. As with implants 10 and 20, the implant 30 has a longitudinally flexible body comprising two longitudinally flexible rods 31. Again, the longitudinally flexible rods 31 may be constructed of wire or may be wire-like and are longitudinally flexible to allow the implant to be threaded through the Schlemm's Canal.

The implant 30 has a series of penetrating members, with each penetrating member having two supporting arms 33 and a penetrating tip 34. The supporting arms 33 are hingedly connected to the flexible rods 31 at hinges 32. Each supporting arm 33 extends between its respective penetrating tip 34 and its respective longitudinally flexible rod 31 and is connected to its respective the longitudinally flexible rod at the hinge 32. As can be seen with implant 30, the supporting arms 33 need not be straight and may be bent or otherwise geometrically shaped to provide the desired result.

The implant 30 is illustrated with its longitudinally flexible rods 31 joined at the distal end of the implant 30 at end 35 and joined at the proximal end of the implant 30 at end 36.

Figure 22:
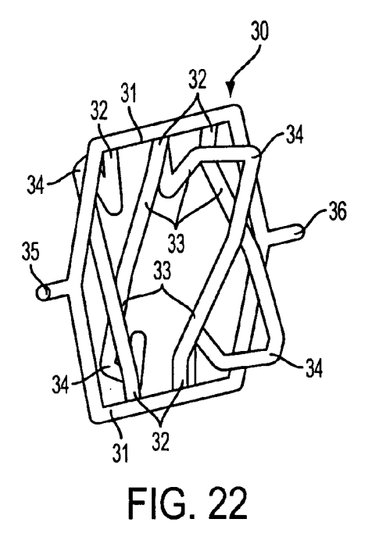
FIG. 22 is a perspective view of a third embodiment of an implant with the penetrating members shown in an unextended position.
Figure 23:
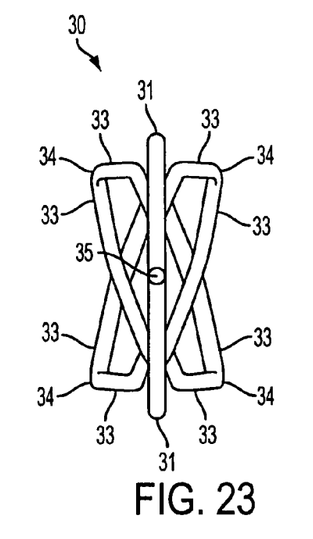
FIG. 23 is an end view of the implant of FIG. 22.

The implant 30 is configured such that in the as-manufactured, relaxed stated of the implant, the penetrating members are in the unextended position, and the penetrating members generally point in a proximal direction along the longitudinal axis of the implant. Thus, as shown in FIGS. 22 and 23, the penetrating members generally point toward the end 36 at the proximal end of the implant 30. In this configuration, advancing the implant 30 in a distal direction through the Schlemm's Canal does not cause the penetrating members to become extended. However, retracting the implant 30 in a proximal direction back through the Schlemm's Canal causes the penetrating members to get caught by the tissue of the walls of the Schlemm's Canal. Further retraction of the implant 30 by pulling on end 36 causes the penetrating members to rotate about hinges 32, thereby moving the penetrating members from the unextended position to the extended position.

Figure 24:
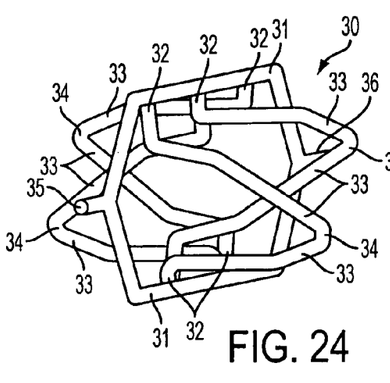
FIG. 24 is a perspective view of the implant of FIG. 22 with the penetrating members shown in an extended position.
Figure 25:
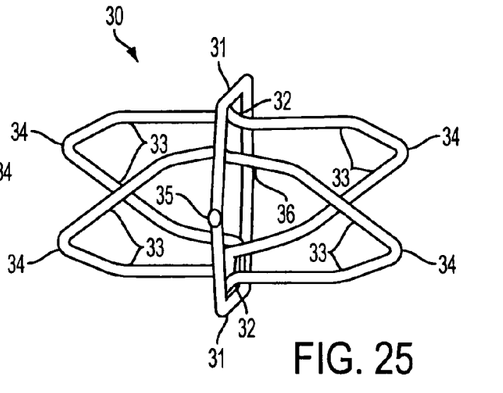
FIG. 25 is an end view of the implant of FIG. 24.

FIGS. 22 and 23 show the implant 30 with the penetrating members in an unextended position. FIGS. 24 and 25 show the implant 40 with the penetrating members in an extended position. As illustrated in FIGS. 22 and 23, when the penetrating members are in the unextended position, the penetrating members and the longitudinally flexible body lie substantially in a single plane, although the profile is slightly larger than that of the implants 10 and 20. This is because the penetrating members in implant 30 stick out a little bit so as to catch on the Schlemm's Canal wall upon retraction on the implant body. Nevertheless, in this example, when the supporting arms 33 and penetrating tips 34 are in the unextended position, the supporting arms 33, the penetrating tips 34, and the longitudinally flexible rods 31 all lie substantially in a single plane, as can be seen in the end view of FIG. 23.

Figure 26:
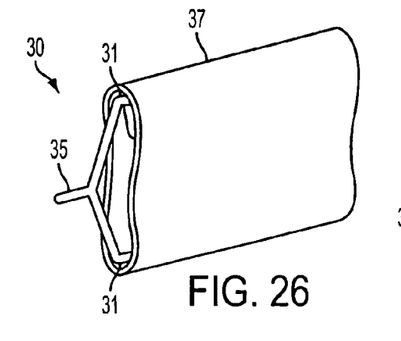
FIG. 26 is a perspective view of the implant of FIG. 22 being inserted within the Schlemm's Canal.

In use, the implant 30 is inserted into the Schlemm's Canal through an access opening, which may be formed ab externo or ab interno as described above. FIG. 26 illustrates the implant 30 being inserted within the Schlemm's Canal 37.

As with the implants 10 and 20, the implant 30 is advanced around at least a substantial portion of the Schlemm's Canal. In this embodiment, the penetrating members are in the unextended position in their relaxed state as manufactured, so there is no need for a sheath to hold the penetrating members in the unextended position. Because of the orientation of the penetrating members of implant 30, advancing the implant 30 distally, with end 35 as the leading end in the direction of travel, allows the penetrating members to simply pass against the wall of the Schlemm's Canal without getting caught. Again, as with implants 10 and 20, implant 30 may be advanced substantially 360 degrees around the Schlemm's Canal or only part way around the Schlemm's Canal, in which case multiple implants may be used.

Figure 27:
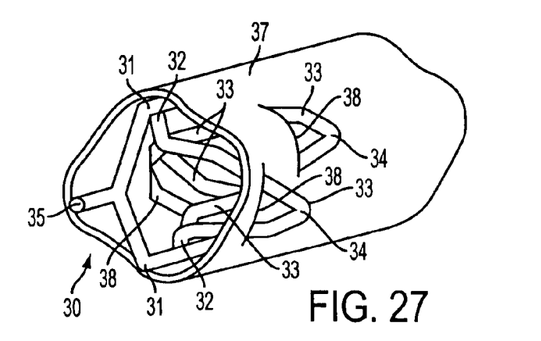
FIG. 27 is a perspective view of the implant of FIG. 26 inside the Schlemm's Canal after deployment of the penetrating members to the extended position.

After the implant 30 is advanced around the Schlemm's Canal as desired, the implant 30 is pulled proximally back through the Schlemm's Canal by pulling end 36, with end 36 as the leading end in the direction of travel. In this direction, the penetrating tips 34 get caught on the wall of the Schlemm's Canal. Further proximal pulling of end 36 causes the penetrating members to rotate at hinges 32, causing the penetrating members to move from the unextended position to the extended position. The hinging motion causes plastic deformation of the implant 30 so that the penetrating members remain in the extended position after the implant is released.

As shown in FIGS. 26 and 27, when the penetrating members move from the unextended position to the extended position, the penetrating members penetrate the wall of the Schlemm's Canal 37. This creates fluid passageways or openings 38 in the wall of the Schlemm's Canal 37. As with implants 10 and 20, the placement of the implant 30 within the Schlemm's Canal can also serve to keep the Schlemm's Canal open. In this regard, the implant can serve as a support scaffolding to maintain the patency of the Schlemm's Canal. The size of the implant 30 may be similar to that of implants 10 and 20.

Figure 28:
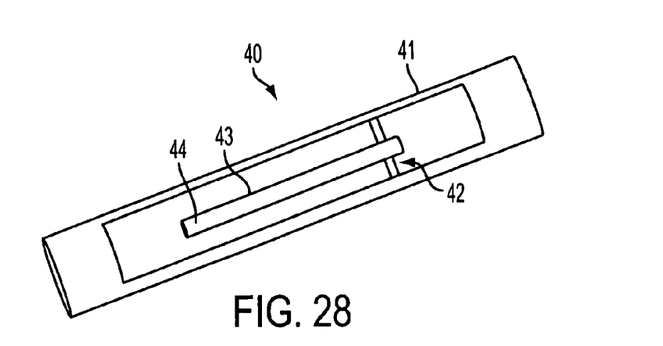
FIG. 28 is a perspective view of a fourth embodiment of an implant with each penetrating member comprising a single supporting arm.
Figure 29:
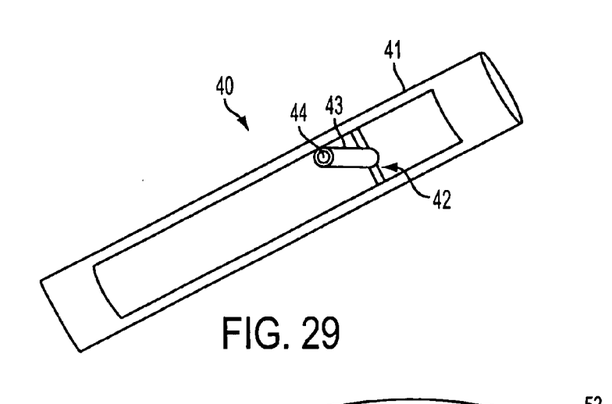
FIG. 29 is a perspective view of the implant of FIG. 29 with the penetrating member shown in an extended position.

FIGS. 28-29 illustrate a fourth embodiment of an implant. The implant 40 in this embodiment has a longitudinally flexible body which may be in the form, for example, of generally tubular shaped structure 41. In this embodiment, each penetrating member comprises one supporting arm 43 terminating in a penetrating tip 44. Although only one supporting arm 43 is illustrated, it will be appreciated that the implant may have a series of such supporting arms 43. In this illustrated example, each supporting arm 43 is in the form of a tube providing a conduit for fluid flow. Thus, when the penetrating tip 44 penetrates the tissue, the tube opening provides an opening through the tissue for fluid flow. In the illustrated embodiment, the supporting arm 43 is connected to the longitudinally flexible body at a hinge 42.

FIG. 28 shows the implant 40 with the penetrating member in an unextended position. In this embodiment, when the penetrating members are in an unextended position, the end view of the implant 40 resembles a single rod. FIG. 29 shows the implant 40 with the penetrating member in an extended position. The penetrating members may be deployed to the extended position by mechanical means, such as a wire or strand, or the penetrating members may be configured to self-expand from the unextended position to the extended position.

The implant 40 may be sized similarly to the implants described above and may be configured to extend part or all of the way around the Schlemm's Canal. The implant 40 is implanted in a similar manner as discussed above. When implanted within the Schlemm's Canal, the implant 40 can create fluid passageways into the Schlemm's Canal through the trabecular meshwork and/or out of the Schlemm's Canal to the collector channels and into the sclera.

An implant in accordance with embodiments of the invention may be made of any of a number of biocompatible materials. For example, the implant may be made of a type of nickel-titanium alloy, cobalt-chrome alloy or stainless steel such as SS316L. The implant may also be coated with a therapeutic agent such that the therapeutic agent elutes from the implant after implantation. Various therapeutic agents may be used. For example, some therapeutic agents that may be desirable for certain applications include heparin, antibiotic drugs, anti-glaucoma drugs, or any other suitable drug or drug combination. The method of coating the implant may be any method as generally known in the art for applying coating to an implant, such as employed in the field of coronary stents. In an alternative embodiment the implant may be made of a biodegradable material, which may be coated or impregnated with a therapeutic agent.

Figure 30:
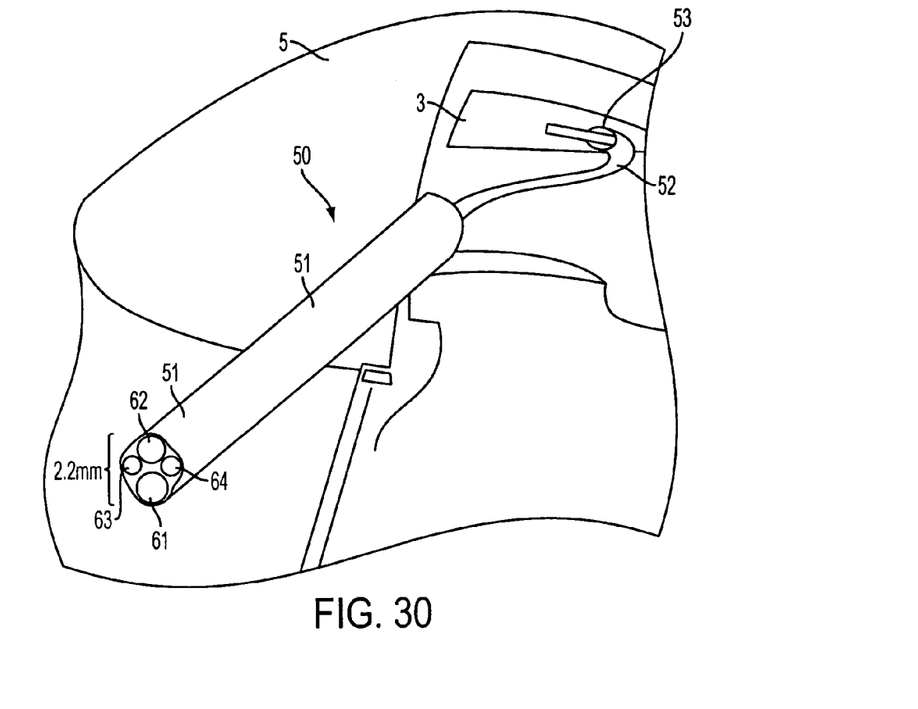
FIG. 30 is a perspective view of a delivery device being used to insert an implant within the Schlemm's Canal.

FIG. 30 is a perspective view of a delivery device 50 that may be used to insert an implant, such as an implant as described above, within the Schlemm's Canal 3. The delivery device may comprise a generally longitudinally extending shaft 51, a hooked end 52 with a piercing tip 53 extending generally perpendicular to the shaft 51, and a lumen 61 passing through the longitudinally extending shaft and the hooked end for accommodating an implant. The delivery device may further comprises one or more lumens 62, 63, 64 for viscoelastic injection, an imaging device, a light source, an operating instrument, and/or irrigation.

In a procedure as illustrated in FIG. 30, a small slit or opening is made in the cornea 5. The delivery device 40 is advanced through the slit or opening in the cornea 5 and the piercing tip is used to create an access passageway from the anterior chamber through the trabecular meshwork to the Schlemm's Canal 3. An imaging device and light source may be used to visualize the area. Irrigation may be used to wash the area. The implant is advanced from a lumen of the delivery device and passed into the Schlemm's Canal. Further implantation proceeds as described above. Before, during or after threading the implant through the Schlemm's Canal, a viscoelastic material, such as sodium hyaluronate, may be injected into the Schlemm's Canal as is known in the art. During the implantation procedure, other surgical instruments may be used through the lumens 62, 63, 64, such as a blade, scissors, coagulator, forceps, needle or another surgical tool. After the implant is in place, the delivery device is withdrawn from the eye. Then, the cornea can be sutured to close the slit or opening.

An implant having a structure and deployment characteristics as described herein has other applications aside from use within the Schlemm's Canal. The implant may be used in other body lumens where opening and/or scaffolding the lumen is desired. For example, the implant may be used as a stent in the vasculature or other body lumens. Depending on the application, the implant may be modified. For example, its size will be tailored to the desired application. In addition, the penetrating members may be designed as support members such that they hold a lumen open but do not penetrate the lumen wall.

As will be appreciated by persons having ordinary skill in the art, the various embodiments of implants, delivery devices and methods described hereinabove are given by way of example only. Various changes, modifications and variations may be applied to the described embodiments without departing from the scope of the invention, defined by the appended claims.

The invention claimed is:

1. A method of implanting an implant for assisting drainage of aqueous humor from the eye, said method comprising:
using an implant sized to fit within the Schlemm's Canal of the eye, said implant having a longitudinal axis and comprising a plurality of penetrating members, wherein each of said penetrating members has a first unextended position in which said penetrating member lies generally close to said longitudinal axis of the implant and a second extended position in which said penetrating member is extended outward to be farther away from the longitudinal axis of the implant;
forming an access opening into the Schlemm's Canal;
inserting said implant into the Schlemm's Canal through said opening;
advancing said implant in a circumferential direction around at least a substantial portion of said Schlemm's Canal with said penetrating members in said first unextended position; and
causing said penetrating members to move from said first unextended position to said second extended position, wherein said penetrating members penetrate the wall of the Schlemm's Canal.

2. The method of claim 1, wherein the step of advancing said implant involves advancing said implant approximately 360 degrees around the Schlemm's Canal.

3. The method of claim 1, wherein the step of forming an access opening into the Schlemm's Canal involves forming an access opening from the outside of the eye under a scleral flap.

4. The method of claim 1, wherein the step of forming an access opening into the Schlemm's Canal involves forming an access opening from the inside of the eye by forming an incision in the cornea and accessing the Schlemm's Canal from the anterior chamber of the eye.

5. The method of claim 1, further comprising delivering the implant to the opening in the Schlemm's Canal by a delivery device comprising a generally longitudinally extending shaft with a piercing tip and a lumen passing through said longitudinally extending shaft for accommodating an implant.

6. The method of claim 1, wherein said penetrating members are configured to self-expand from said first unextended position to said second extended position, and wherein the step of causing said penetrating members to move from said first unextended position to said second extended position involves allowing the penetrating members to self-expand.

7. The method of claim 1, wherein the penetrating members comprise a resilient material, wherein in an unconstrained state said penetrating members are in said second extended position, and wherein in a constrained state said penetrating members are held in said first unextended position.

8. The method of claim 7, further comprising a sheath around the implant wherein said sheath holds the penetrating members in said first unextended position, and wherein the step of causing said penetrating members to move from said first unextended position to said second extended position involves withdrawing the sheath.

9. The method of claim 1, wherein the penetrating members comprise a shape memory material, wherein the heat from the eye causes the penetrating members to move from the first unextended position to the second extended position.

10. The method of claim 1, wherein said implant comprises a deployment rod attached to said penetrating members, and wherein the step of causing said penetrating members to move from said first unextended position to said second extended position involves actuation of said deployment rod.

11. The method of claim 1, wherein said implant comprises a longitudinally flexible body, wherein each penetrating member comprises at least one penetrating tip, wherein each penetrating member further comprises at least one supporting arm connecting the penetrating tip to the longitudinally flexible body at a hinge, wherein said implant comprises a deployment rod attached to said penetrating members, and wherein the step of causing said penetrating members to move from said first unextended position to said second extended position involves actuation of said deployment rod.

12. The method of claim 11, wherein actuation of said deployment rod is performed by moving said deployment rod relative to said longitudinally flexible body.

13. The method of claim 1, wherein when said penetrating members are in said first unextended position, said penetrating members generally point in a proximal direction along the longitudinal axis of the implant, wherein advancing the implant in a distal direction does not cause said penetrating members to become extended, and wherein retracting the implant in a proximal direction back through the Schlemm's Canal causes said penetrating members to move from the first unextended position to the second extended position.

14. A method of implanting an implant for assisting drainage of aqueous humor from an eye, said method comprising:
using an implant sized to fit within the Schlemm's Canal of the eye, the Schlemm's Canal generally encircling the anterior chamber of the eye in a circumferential direction, said implant having a longitudinal axis and comprising a plurality of penetrating members, wherein each of said penetrating members has a first unextended position in which said penetrating member lies generally close to said longitudinal axis of the implant and a second extended position in which said penetrating member is extended outward to be farther away from the longitudinal axis of the implant;

forming an access opening into the Schlemm's Canal;

inserting said implant into the Schlemm's Canal through said opening;

advancing said implant in the circumferential direction around at least a substantial portion of the Schlemm's Canal with said penetrating members in said first unextended position; and causing said penetrating members to move from said first unextended position to said second extended position, wherein said penetrating members penetrate the wall of the Schlemm's Canal.

15. The method of claim 14, wherein the step of advancing said implant involves advancing said implant approximately 360 degrees around the Schlemm's Canal.

16. The method of claim 14, wherein the step of forming an access opening into the Schlemm's Canal involves forming an access opening from the outside of the eye under a scleral flap.

17. The method of claim 14, wherein the step of forming an access opening into the Schlemm's Canal involves forming an access opening from the inside of the eye by forming an incision in the cornea and accessing the Schlemm's Canal from the anterior chamber of the eye.

18. The method of claim 14, wherein said implant comprises a deployment rod attached to said penetrating members, and wherein the step of causing said penetrating members to move from said first unextended position to said second extended position involves actuation of said deployment rod.

19. The method of claim 14, wherein said implant comprises a longitudinally flexible body, wherein each penetrating member comprises at least one penetrating tip, wherein each penetrating member further comprises at least one supporting arm connecting the penetrating tip to the longitudinally flexible body at a hinge, wherein said implant comprises a deployment rod attached to said penetrating members, and wherein the step of causing said penetrating members to move from said first unextended position to said second extended position involves actuation of said deployment rod.

20. The method of claim 14, further comprising, prior to the step of inserting said implant into the Schlemm's Canal through said opening, the steps of:

inserting a guide wire or strand into the Schlemm's Canal;

advancing said guide wire or strand around the Schlemm's Canal such that a leading edge of the guide wire or strand emerges from the Schlemm's Canal in the area of the opening;

attaching the implant to the guide wire or strand; and withdrawing the guide wire or strand back through the Schlemm's Canal, thereby pulling the implant to perform the steps of inserting said implant into the Schlemm's Canal and advancing said implant around at least a substantial portion of the Schlemm's Canal.

\* \* \* \* \*